US010398361B2

(12) United States Patent
Karpiloff

(10) Patent No.: US 10,398,361 B2
(45) Date of Patent: Sep. 3, 2019

(54) LOW COST BLOOD COLLECTION SET USING BLISTER PACKAGE

(71) Applicant: Becton, Dickinson and Company, Franklin Lakes, NJ (US)

(72) Inventor: Kenneth Karpiloff, Mamaroneck, NY (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 634 days.

(21) Appl. No.: 13/737,180

(22) Filed: Jan. 9, 2013

(65) Prior Publication Data

US 2013/0178759 A1 Jul. 11, 2013

Related U.S. Application Data

(60) Provisional application No. 61/584,967, filed on Jan. 10, 2012.

(51) Int. Cl.
*A61B 5/15* (2006.01)
*A61M 5/00* (2006.01)
*A61B 5/154* (2006.01)

(52) U.S. Cl.
CPC .......... *A61B 5/1405* (2013.01); *A61B 5/1438* (2013.01); *A61B 5/15003* (2013.01); *A61B 5/154* (2013.01); *A61B 5/150305* (2013.01); *A61B 5/150496* (2013.01); *A61B 5/150557* (2013.01); *A61B 5/150732* (2013.01); *A61M 5/002* (2013.01); *A61B 5/150389* (2013.01); *A61B 5/150572* (2013.01); *A61B 5/150717* (2013.01); *Y10T 29/49826* (2015.01)

(58) Field of Classification Search
CPC ........ A61B 5/150305; A61B 5/150557; A61B 5/150732; A61B 5/150534; A61B 5/150572; A61B 5/150717; A61B 5/1405; A61B 5/154; A61B 5/150496; A61B 5/15003; A61B 5/1438; A61B 5/150389; A61M 5/002
USPC .................. 600/576, 580, 581; 206/364–366
See application file for complete search history.

(56) References Cited

U.S. PATENT DOCUMENTS

| | | | | | |
|---|---|---|---|---|---|
| 2,953,243 | A | * | 9/1960 | Roehr | ........................ 206/216 |
| 3,074,540 | A | * | 1/1963 | Beich | .................... A61M 5/002 |
| | | | | | 206/366 |
| 3,075,639 | A | * | 1/1963 | Lingley | ........................ 206/366 |
| 3,677,245 | A | * | 7/1972 | Welch | .......................... 604/193 |
| 4,091,922 | A | * | 5/1978 | Egler | .................. A61M 25/002 |
| | | | | | 206/364 |

(Continued)

*Primary Examiner* — David J. McCrosky
(74) *Attorney, Agent, or Firm* — The Webb Law Firm

(57) ABSTRACT

A low cost fluid collection set having an integrated package including a needle cannula having a first end and a second end, a hub configured for supporting the needle cannula, and a package at least partially enclosing the needle cannula and the hub is disclosed. The package includes at least one openable region configured for receiving a fluid collection device therein wherein this openable region is in communication with at least one of the first end or the second end of the needle cannula and wherein the package is configured to be used as a holding device to manipulate the needle cannula during fluid collection. The package also functions as a shield for the first end of the needle cannula after use. A method of using the fluid collection set having an integrated package and a method of making the fluid collection set is provided.

18 Claims, 10 Drawing Sheets

(56) References Cited

U.S. PATENT DOCUMENTS

| | | | |
|---|---|---|---|
| 4,150,666 A | | 4/1979 | Brush |
| 4,184,593 A | | 1/1980 | Dorr |
| 4,236,636 A | * | 12/1980 | Kuchenbecker ..... B65D 75/368 |
| | | | 206/461 |
| 4,886,071 A | * | 12/1989 | Mehl et al. .................. 600/573 |
| 4,991,601 A | | 2/1991 | Kasai et al. |
| 5,083,671 A | * | 1/1992 | Hayes .................. B65D 50/061 |
| | | | 215/224 |
| 5,181,524 A | * | 1/1993 | Wanderer ........... A61B 5/15003 |
| | | | 600/577 |
| 5,222,947 A | * | 6/1993 | D'Amico ............ A61M 5/3129 |
| | | | 604/198 |
| 5,236,749 A | * | 8/1993 | Ewing .................... B65D 75/36 |
| | | | 428/137 |
| 5,407,070 A | * | 4/1995 | Bascos .................. A61M 5/002 |
| | | | 206/364 |
| 5,487,734 A | * | 1/1996 | Thorne et al. ................. 604/195 |
| 5,607,402 A | * | 3/1997 | Dufresne ......... A61B 5/150305 |
| | | | 604/110 |
| 5,715,833 A | * | 2/1998 | Kleinhappl .................... 600/516 |
| 5,895,374 A | * | 4/1999 | Rodsten ............. A61M 25/002 |
| | | | 206/364 |
| 6,010,462 A | * | 1/2000 | Stoermer, III .......... B65B 9/042 |
| | | | 206/363 |
| 6,017,317 A | | 1/2000 | Newby et al. |
| 6,358,241 B1 | * | 3/2002 | Shapeton et al. .................. 606/1 |
| 6,994,213 B2 | * | 2/2006 | Giard, Jr. ............ A61M 25/002 |
| | | | 206/363 |
| 2006/0247555 A1 | * | 11/2006 | Harttig ............... A61B 5/15142 |
| | | | 600/584 |
| 2006/0282045 A1 | * | 12/2006 | Wilkinson et al. ........... 604/198 |

\* cited by examiner

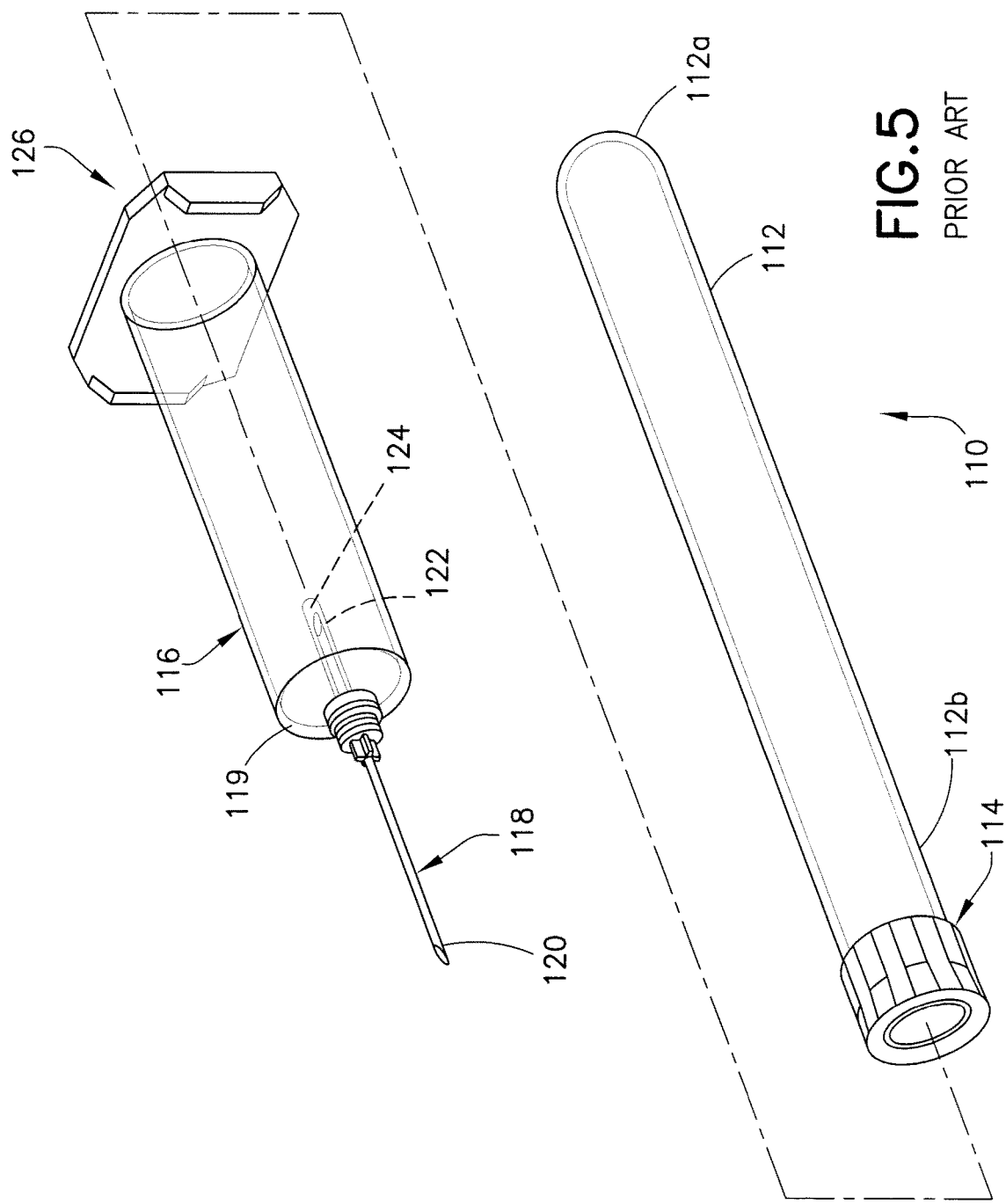

LOW COST BLOOD COLLECTION SET USING BLISTER PACKAGE

CROSS-REFERENCE TO RELATED APPLICATION

The present application claims priority to U.S. Provisional Application No. 61/584,967, filed Jan. 10, 2012, entitled "Low Cost Blood Collection Set Using Blister Package", the entire disclosure of which is hereby incorporated by reference.

BACKGROUND OF THE INVENTION

Field of the Invention

This invention relates to a low cost blood collection set and, more particularly, to an integrated low cost blood collection set and package wherein the package forms the holder for manipulation of the needle cannula and also forms the shield for enclosing the needle cannula after use.

Description of Related Art

Blood collection tubes are commonly used by doctors, nurses, and other medical personnel to draw a sample of a body fluid from a patient or to receive a fluid sample from another vessel. Such tubes are ordinarily evacuated, and include a pierceable closure. During one typical use of a blood collection tube, one end, such as the patient end, of a double-ended needle cannula is used to pierce a vein. The evacuated blood collection tube is then urged towards the second end or non-patient end, of the double-ended needle cannula until its closure is pierced. Blood is thereby drawn into the tube.

The double-ended needle cannula is typically mounted to a hub to form a double-ended needle assembly. This double-ended needle assembly is ordinarily mounted to a holder having a tubular body. The blood collection tube is inserted within the tubular body in order to engage the second or non-patient end of the needle cannula. One example of a needle holder assembly and blood collection tube is shown in U.S. Pat. No. 6,017,317, owned by the assignee of the present invention, the entirety of which is hereby incorporated by reference. U.S. Pat. Nos. 4,991,601 and 4,150,666 also disclose various blood collection tubes and/or holders for such tubes.

The double-ended needle assembly and holder are typically packaged in a sterile blister pack. The medical practitioner then removes the holder and needle assembly, inserts the first end or patient end of the needle cannula into a patient, and then inserts a fluid collection tube, such as a vacuum tube, into the holder and into contact with the second or non-patient end of the needle cannula to collect the fluid sample. Safe fluid collection practices include use of a needle shield to cover the needle after use and to allow for proper and sanitary disposal thereof. This shield can be associated with the needle holder or can be a separate member.

Manufacturing costs and packaging of these various members of the fluid collection set can be costly, so that use of the fluid collection set in economically disadvantaged communities is not possible. Oftentimes, the components are separately manufactured and assembled to form the fluid collection set. After assembly, a package is thermoformed about the contours of the holder, needle assembly, and/or the shield to form a sterile blister pack. As a cost-saving measure, these economically disadvantaged communities may attempt to reuse the holder, which could post a health risk to the medical practitioner and/or patient. Also, cross-contamination of a fluid sample could occur due to the reuse of the holder. As another cost-saving measure, a needle shield that may not be used for proper disposal may be eliminated from the collection set.

Accordingly, there is a need in the art that eliminates the need for the manufacturing of these multiple components of the blood collection set and that eliminates the assembly time associated therewith prior to packaging. There is also a need in the art which would prevent reuse of the needle holder and would eliminate the additional costs associated with providing a needle shield.

SUMMARY OF THE INVENTION

The present invention is directed to a low-cost fluid collection set and integrated package assembly that eliminates a separately molded holder, eliminates a separate safety shield, eliminates assembly of the holder and safety shield, and eliminates a separate packaging step for the assembled fluid-collection set.

In accordance with an embodiment of the present invention, a fluid collection set having an integrated package includes a needle cannula having a first end and a second end, a hub configured for supporting the needle cannula, and a package at least partially enclosing the needle cannula and the hub. The package includes at least one openable region configured for receiving a fluid collection device therein, wherein the openable region is in communication with at least one of the first end or the second end of the needle cannula. The package is configured to be used as a holding device to manipulate the needle cannula during fluid collection.

The first end of the cannula can include a patient end and the second end of the cannula can include a non-patient end. The package can be a sterile, thermoformed blister pack. According to certain configurations, the package can include a first portion configured for enclosing the first end of the needle cannula, a second portion configured for receiving the fluid collection device, and a transition portion positioned between the first portion and the second portion. The transition portion can be configured to secure the hub therein. The second portion can comprise a holder for manipulating the needle cannula during fluid collection.

The first portion can include a first openable region and the second portion can include a second openable region, wherein the first openable region provides communication with the first portion and the second openable region provides communication with the second portion. The first and second openable regions can be defined by a frangible portion to facilitate opening thereof. The first portion can be configured for shielding the first end of the needle cannula after use. The package can include at least one undercut portion configured for cooperation with the first portion to snap the first portion in place about the first end of the needle to lock the needle therein.

The hub is secured within the package. The hub can be secured by a variety of techniques including gluing, welding, or mechanical securing, wherein the package is configured to allow for a snap fit within the transition portion of the package.

According to certain configurations, the package includes a back cover and at least a portion of the back cover is removable to provide access to the second end of the needle or to the fluid collection device. According to another configuration, the second openable region can be provided within a back wall portion of the second portion and this region can be defined by a frangible portion that can be punched through to allow access to this second portion.

The fluid collection set can further include an evacuated specimen collection container which is engageable with the second end of the needle cannula through at least a portion of the package. The evacuated specimen collection container can be engageable through the second openable region.

In accordance with another embodiment of the present invention, a method of using a fluid collection set having an integrated package includes providing a package including a needle cannula having a first end and a second end, and a hub configured for supporting the needle cannula, opening the package at a first openable region to expose the first end of the needle cannula, inserting the first end of the needle cannula into a patient, and opening the package at a second openable region and receiving a fluid collection device therein, wherein the second openable region is in communication with the second end of the needle cannula. The method further includes inserting the fluid collection device into the second openable region such that it engages the second end of the needle cannula to withdraw a fluid sample from the patient, wherein the package is configured to be used as a holding device to manipulate the needle cannula during fluid collection.

In certain configurations, the fluid collection device comprises an evacuated specimen collection container engageable with the second end of the needle cannula through at least a portion of the package. The method further includes withdrawing the first end of the needle cannula from the patient and closing the package to shield the first end of the needle cannula therein for disposal. The package can include undercut portions adjacent the first end of the needle cannula to at least partially trap the needle cannula inside the package after use. The package can comprise a sterile, thermoformed blister pack and the second end of the needle cannula can include a pierceable sleeve thereon. The hub can be secured within the package.

In accordance with another embodiment of the present invention, a method of forming a fluid collection set includes thermoforming a blister pack defining a first portion, a second portion, and a transition portion located between the first portion and the second portion, providing a needle hub supporting a needle cannula wherein the needle hub has a first end and a second end, and securing the needle hub within the transition portion of the blister pack such that the first end of the needle cannula extends within the first portion of the blister pack and the second end of the needle cannula extends within the second portion of the blister pack. The first portion has a shape configured to enclose the first end of the needle cannula and the second portion has a shape configured to receive a fluid collection device therein and to function as a needle holder to enable manipulation of the needle cannula during fluid collection. The method further includes providing a first frangible portion adjacent an end of the first portion, wherein the first frangible portion is configured to expose the first end of the needle cannula, and providing a second frangible portion adjacent an end of the second portion, wherein the second frangible portion is configured to receive the fluid collection device therein. The method can also include providing at least one undercut in the first portion configured to cooperate with the blister pack to enclose the first end of the needle cannula after use for disposal of the used fluid collection set.

These and other features and characteristics of the present invention, as well as the methods of operation and functions of the related elements of structures, and the combination of parts and economies of manufacture, will become more apparent upon consideration of the following description with reference to the accompanying drawings, all of which form a part of this specification, wherein like reference numerals designate corresponding parts in the various figures.

BRIEF DESCRIPTION OF THE DRAWINGS

FIG. 5 is a perspective view of an assembly for collecting body fluids and a tube holder capable of receiving a portion of the assembly according to the prior art.

DETAILED DESCRIPTION OF THE INVENTION

Figure 1:
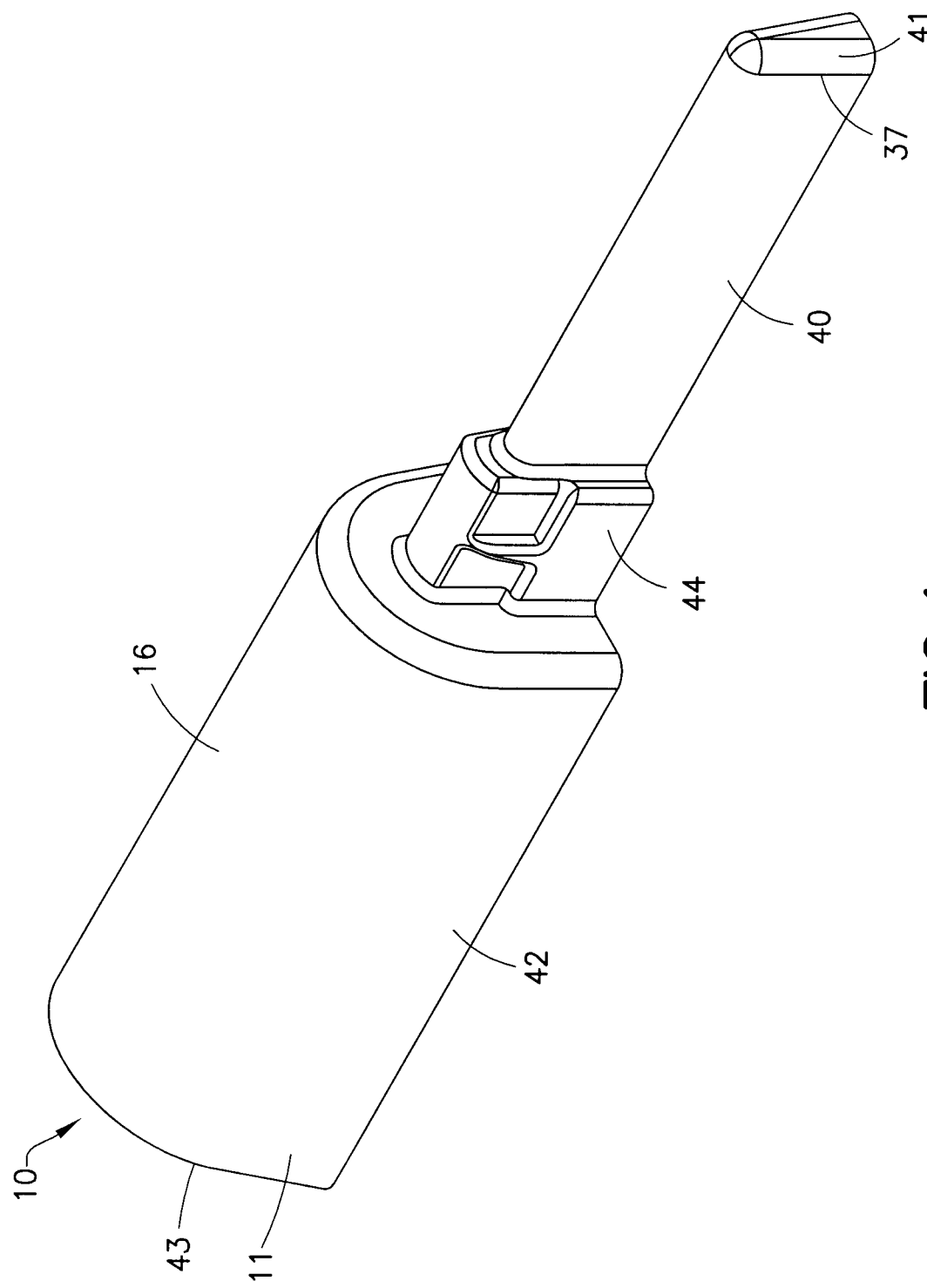
FIG. 1 is a side perspective view of a low cost fluid collection set and blister pack in accordance with an embodiment of the present invention.

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is made to FIG. 5 which shows a perspective view of an assembly, generally indicated as 110, for collecting blood or other body fluids, according to the prior art. The assembly 110 includes a generally cylindrical fluid collection container 112 having a closed end 112a and an open end 112b, and a closure assembly 114 which can be removably mounted to the open end of the container. The collection container 112 can be an evacuated specimen collection container as is known in the art and the closure assembly 114 typically includes a resealable member or gas barrier member (not shown) for maintaining a predetermined vacuum pressure in the collection container 112. The collection container 112 is positioned within a holder 116 to which a double-ended needle assembly 118 is mounted at one end 119 thereof.

With continuing reference to FIG. 5, the double-ended needle assembly 118 includes a first or patient end 120 and a second or non-patient end 122. A sheath or pierceable cover 124 can be located about the second or non-patient end 122 of the needle assembly 118. The holder includes an open end 126 which is configured to receive the collection container 112. In operation, the first or patient end 120 of the needle assembly 118 is inserted into a collection site, such as a patient's vein, and then the collection container 112 is inserted into the holder 116 through open end 126 such that the second or non-patient end 122 of the needle assembly 118 displaced and pierces sheath 124 and subsequently pierces the resealable member and/or gas barrier member of the closure assembly 114. Once the non-patient end 122 is in fluid communication with the collection container 112, the vacuum within the collection container 112 applies a force to the fluid specimen to draw it into the collection container 112.

Figure 2:
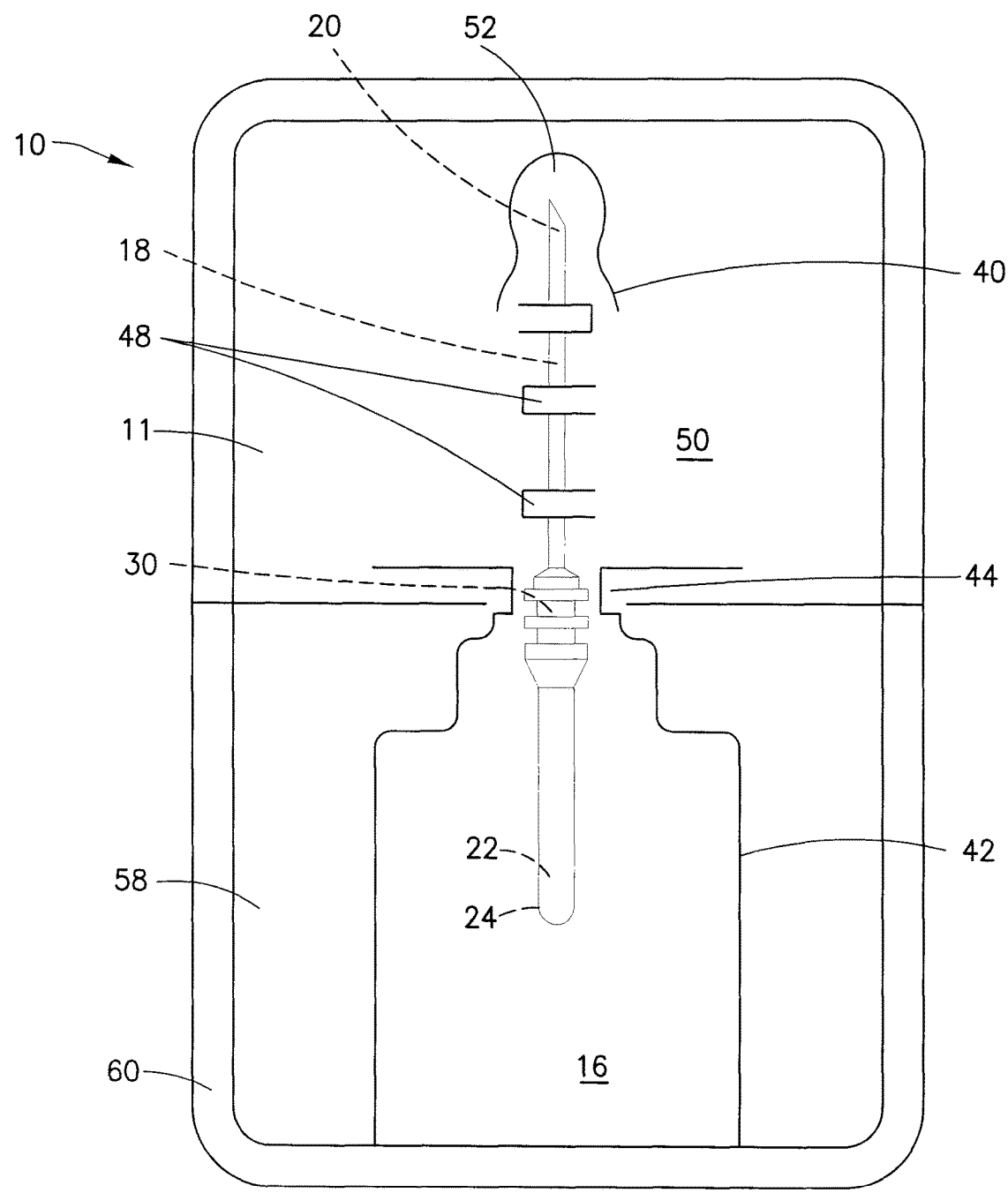
FIG. 2 is a top view of the low cost fluid collection set and blister pack of FIG. 1, showing the needle cannula enclosed therewith in accordance with an embodiment of the present invention.

Reference is now made to FIGS. 1-2 which show a side perspective and top view of a fluid collection set, generally indicated as 10, according to an embodiment of the present invention. The fluid collection set 10 includes an integrated package 11 wherein a portion of the package 16 is in the shape of a needle holder or in the shape of a holding device, which may be used in place of the needle holder 116 of FIG. 5, eliminating the need for this separate needle holder 116 and enabling manipulation of the needle during fluid collection, such as during the withdrawal of blood from a patient or withdrawal of a fluid from another source.

Figure 3A:
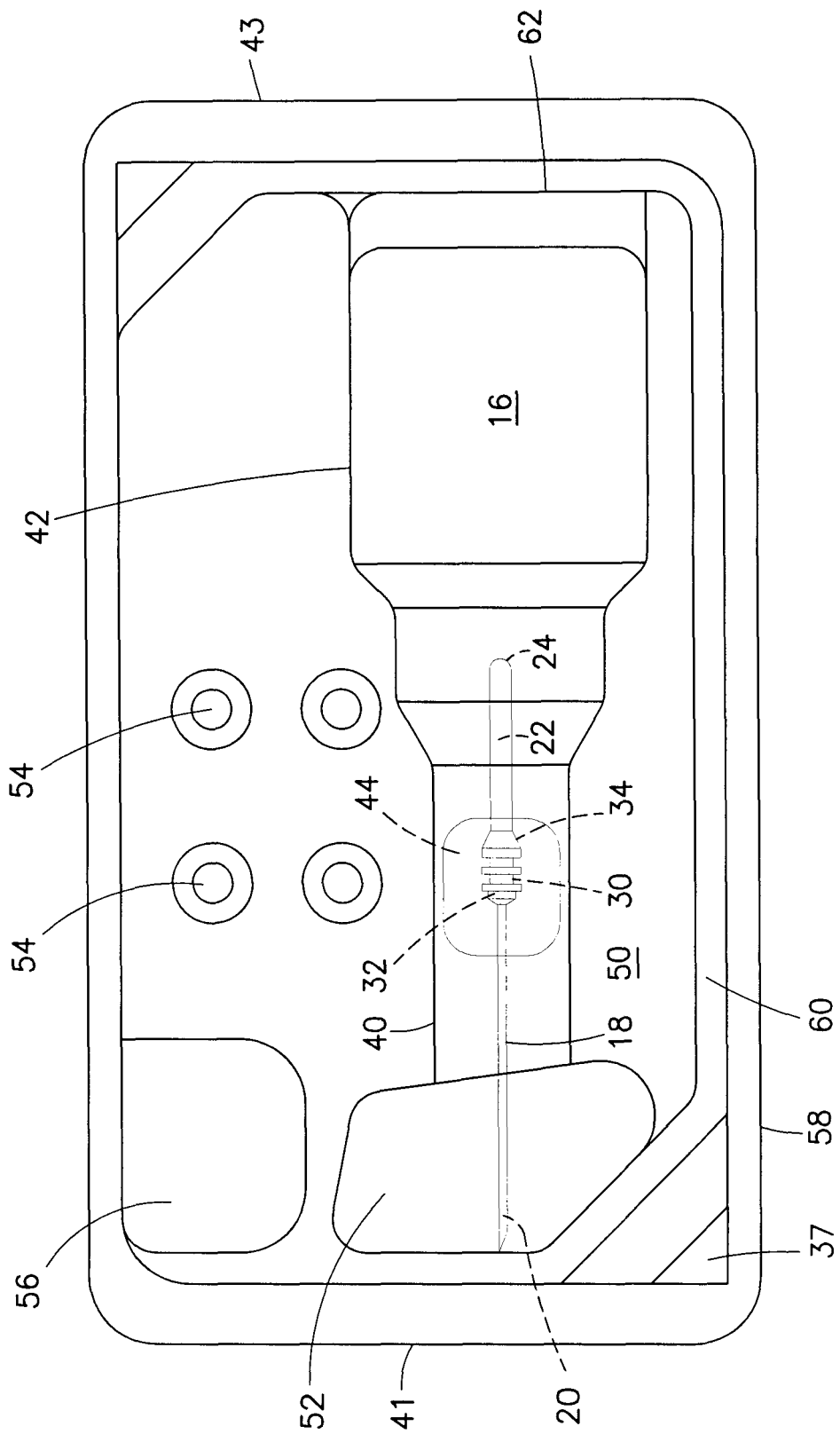
FIG. 3A is a top view of the low cost fluid collection set and blister pack of similar design of FIG. 2 prior to use of the device in accordance with an embodiment of the present invention.
Figure 3B:
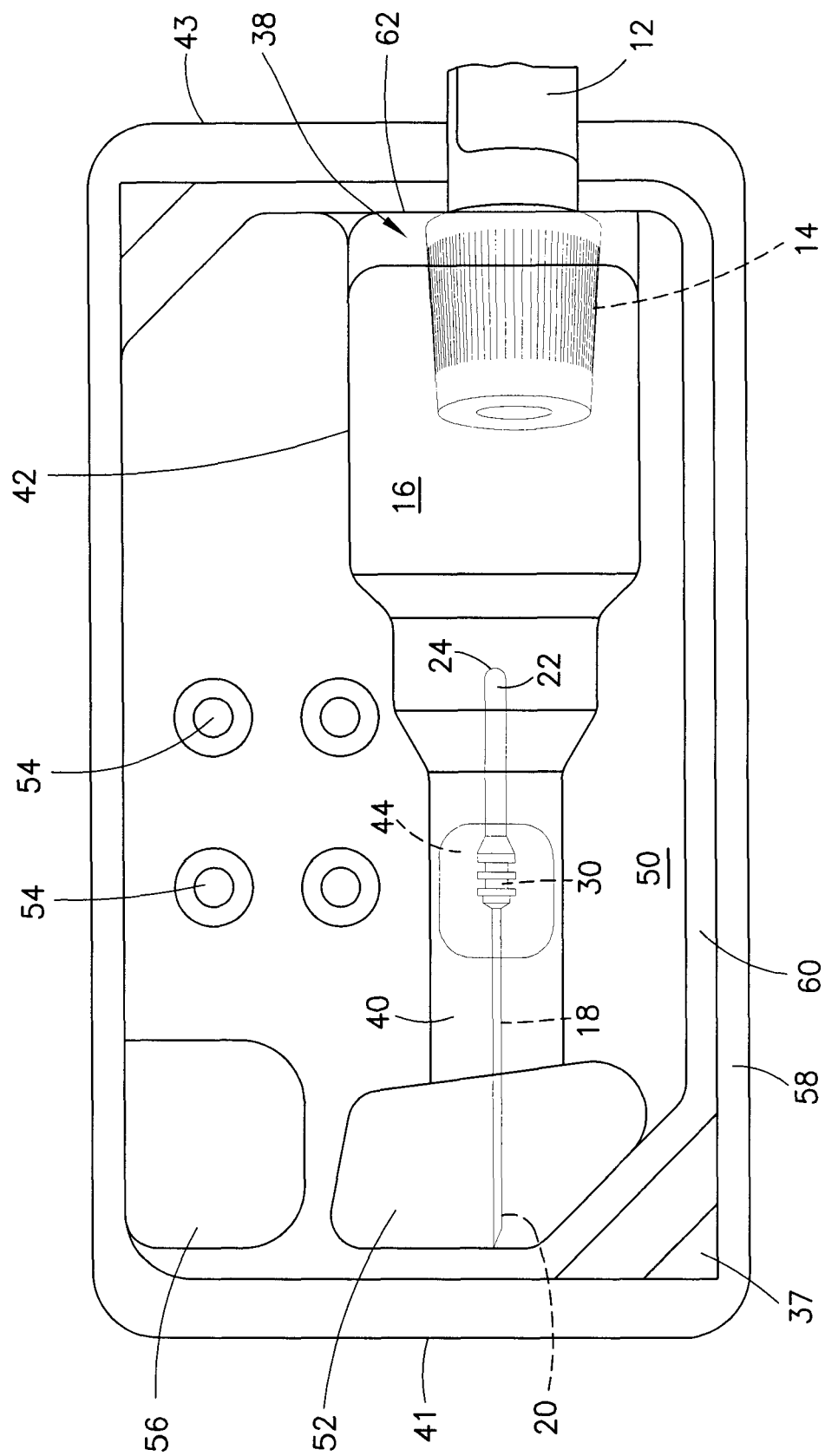
FIG. 3B is a top view of the low cost fluid collection set and blister pack of FIG. 3A showing the insertion of a fluid collection container into the holder portion of the pack in accordance with an embodiment of the present invention.
Figure 3C:
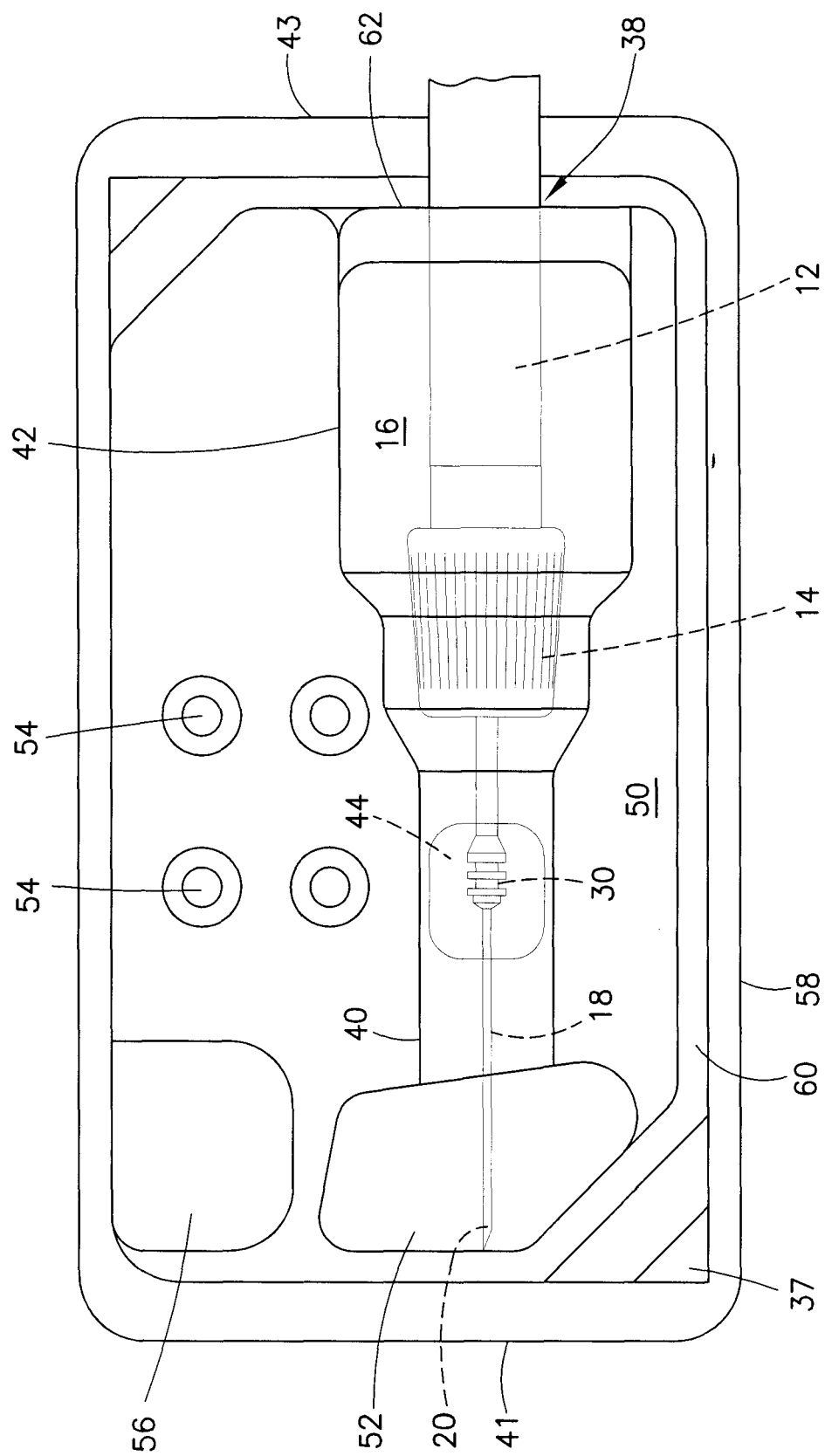
FIG. 3C is a top view of the low cost fluid collection set and blister pack of FIG. 3A showing the interaction of the non-patient end of the needle cannula with the fluid collection container in accordance with an embodiment of the present invention.
Figure 3D:
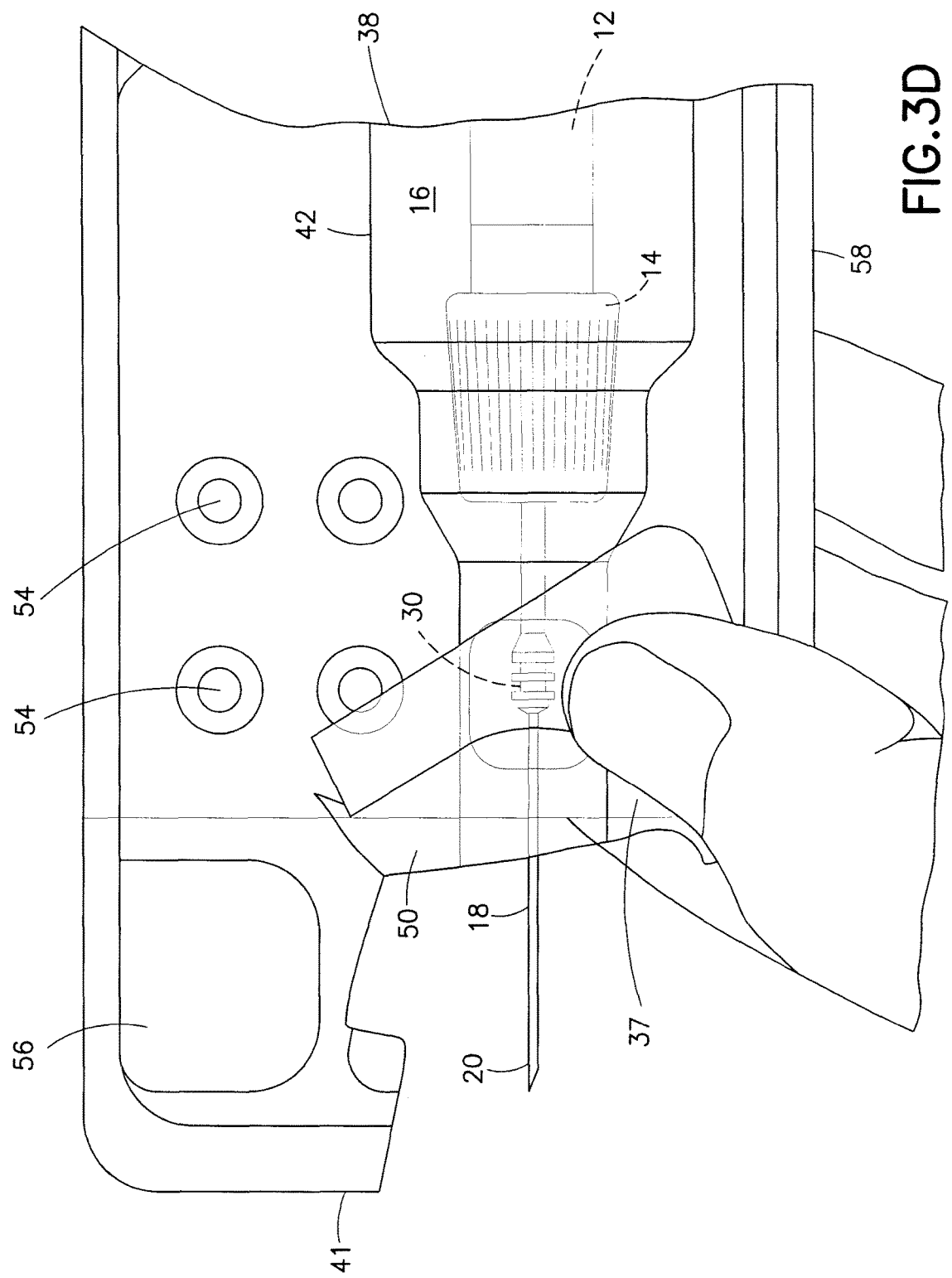
FIG. 3D is a top view of the low cost fluid collection set and blister pack of FIG. 3A showing the exposure of the patient end of the needle cannula in accordance with an embodiment of the present invention.
Figure 3E:
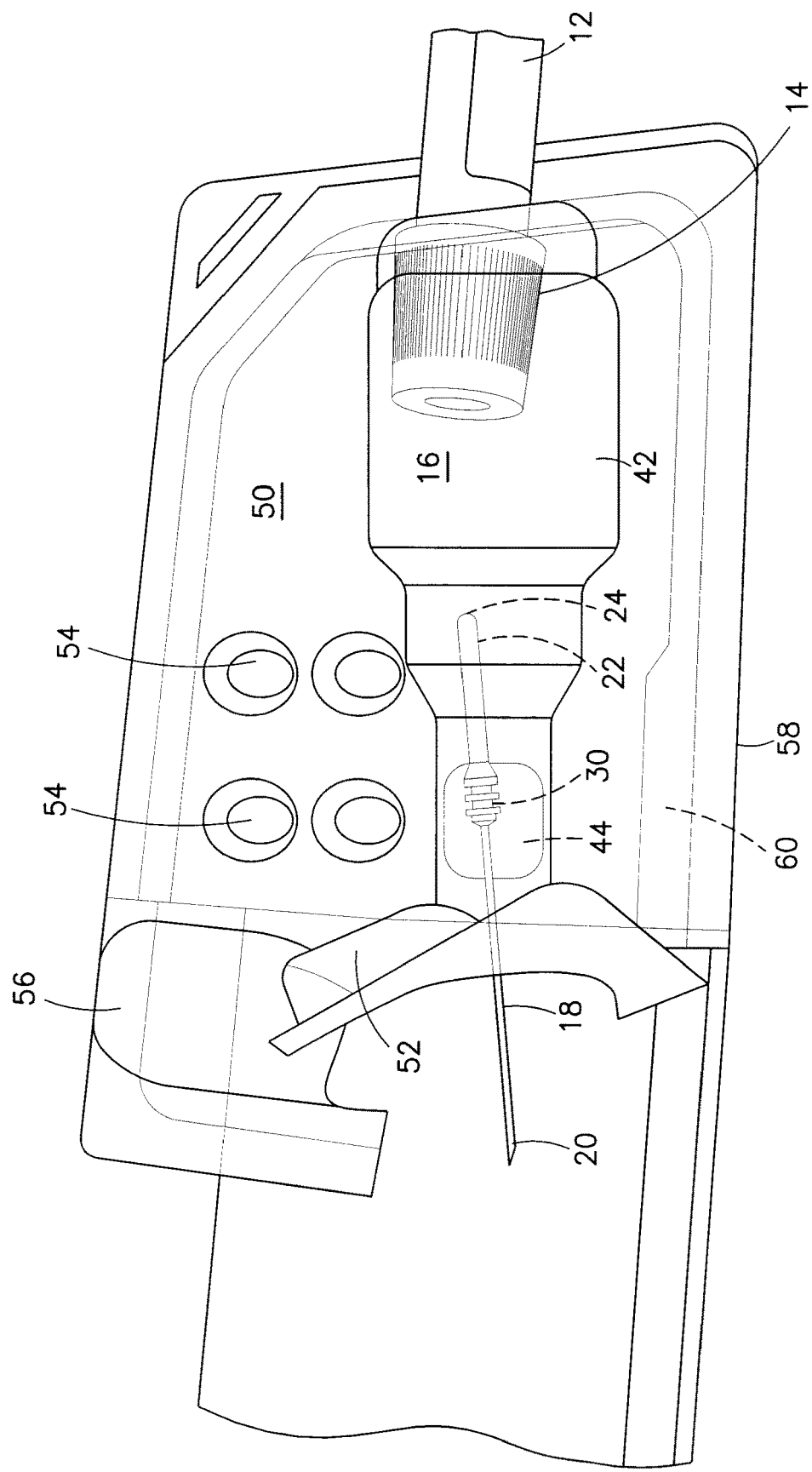
FIG. 3E is a top view of the low cost fluid collection set and blister pack of FIG. 3A showing removal of the fluid collection container after fluid collection in accordance with an embodiment of the present invention.
Figure 3F:
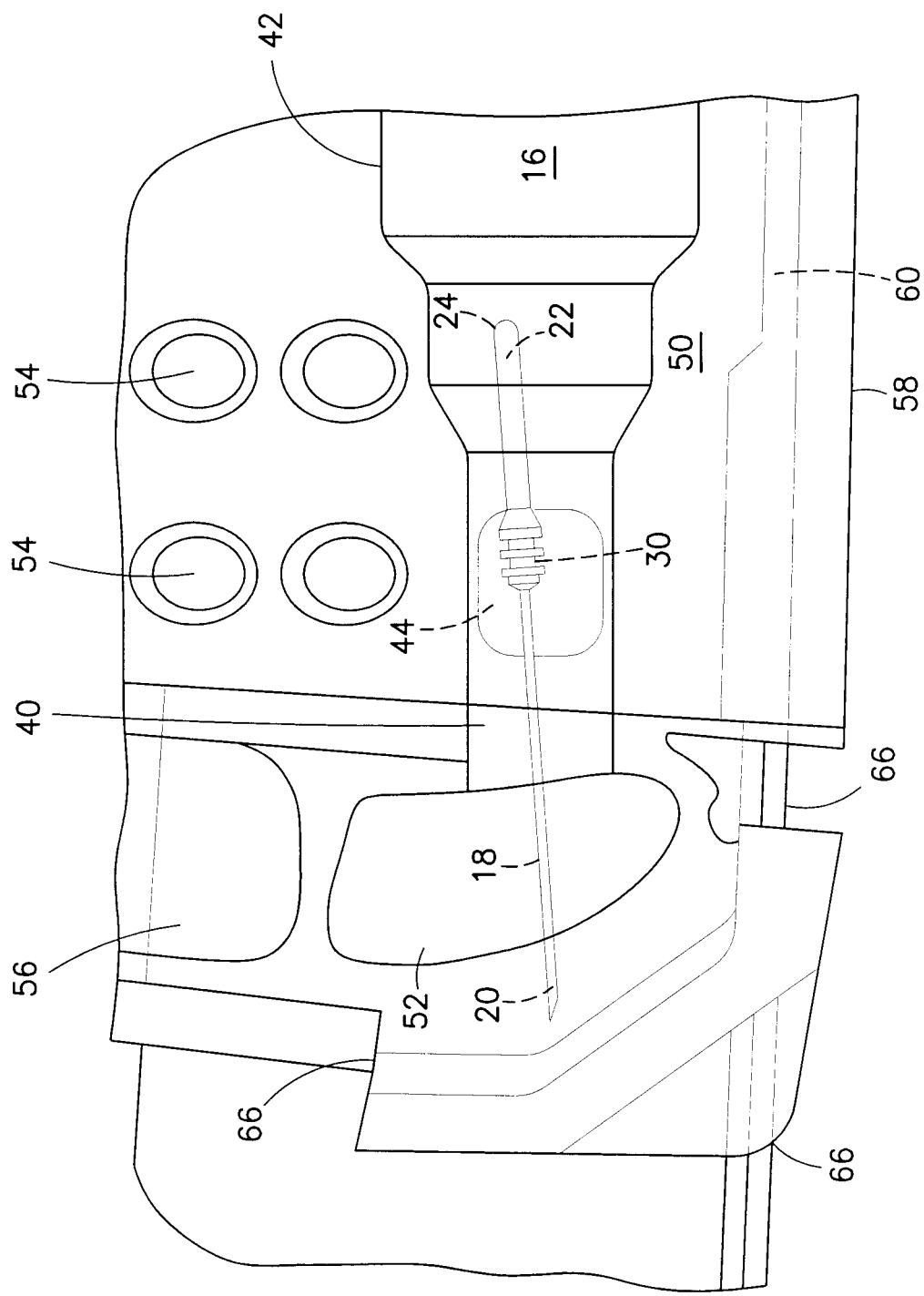
FIG. 3F is a top view of the low cost fluid collection set and blister pack of FIG. 3A showing shielding of the needle with the blister pack after completion of fluid collection in accordance with an embodiment of the present invention.
Figure 4:
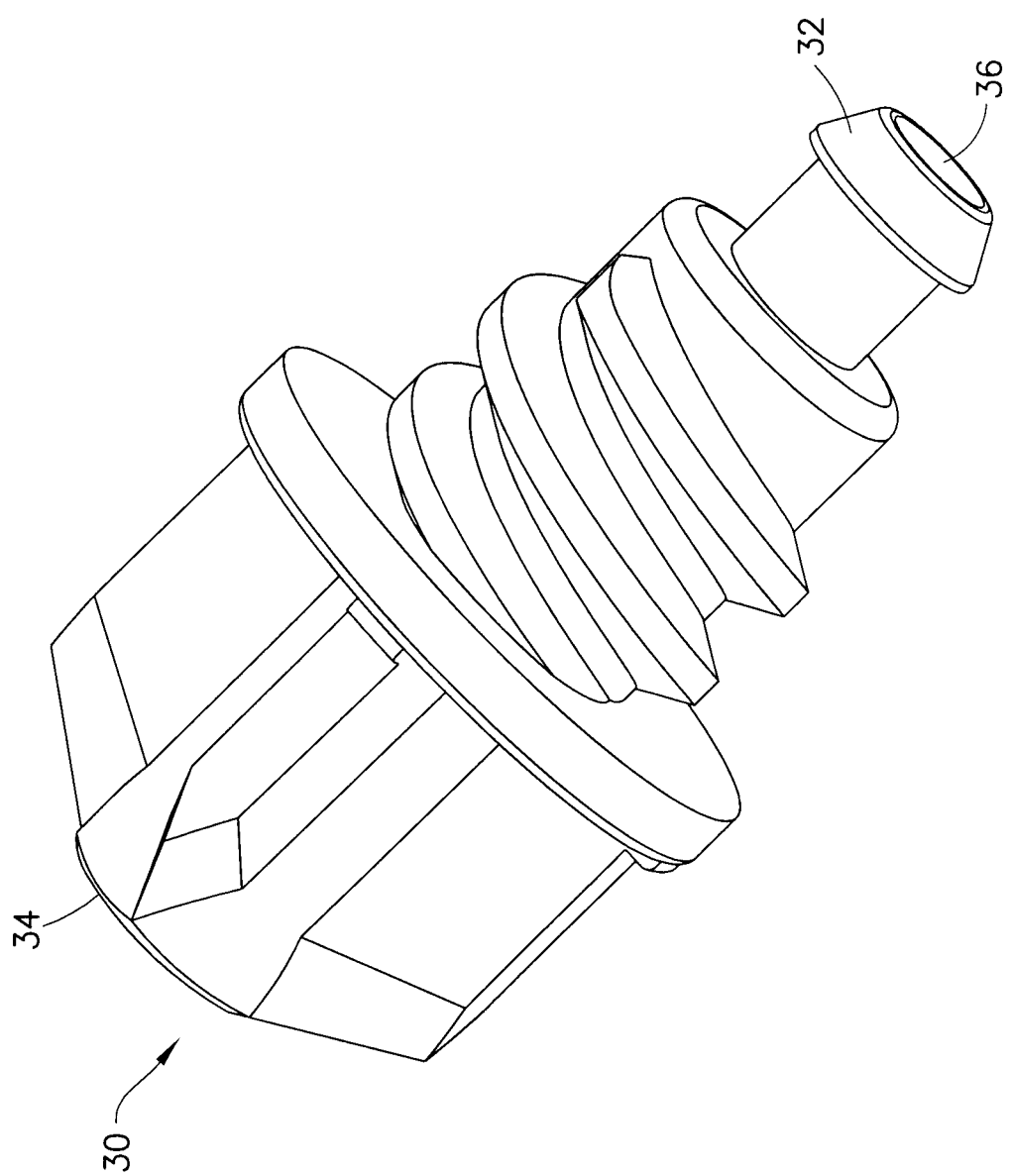
FIG. 4 is a side perspective view of one type of needle hub which can be used with the low cost fluid collection set and blister pack in accordance with an embodiment of the present invention.

With continuing reference to FIGS. 1-2 and with reference to FIGS. 3A-3F and 4, the fluid collection set 10 includes a needle cannula 18 having a first or patient end 20, a second or non-patient end 22, and a lumen extending therebetween. A hub 30, such as shown in detail in FIG. 4, is provided which is configured for supporting the needle cannula 18. It can be appreciated that the hub 30 can be of any known design and that the hub 30 shown in FIG. 4 is only one type of hub that can be used for supporting the needle cannula 18. The hub 30 includes a distal or patient end 32, a proximal or non-patient end 34, and a passage 36 extending between the distal and proximal ends 32, 34. The needle cannula 18 is associated with the hub 30 such that the lumen 28 is located within and extends through the passage 36 of the hub 30 and the first or patient end 20 extends through the distal or patient end 32 of the hub and the second or non-patient end 22 extends through the proximal or non-patient end of the hub 30. A package 11 at least partially encloses the needle cannula 18 and the hub 30. The package 11 includes at least one or a second openable region 38 configured for receiving a fluid collection device or a collection container 12, as shown in FIGS. 3B-3E therein. The openable region 38 is in communication with at least one of the first end 20 or the second end 22 of the needle cannula 18. The package 11 is configured to be used as a holding device to manipulate the needle cannula 18 during fluid collection.

According to one embodiment, the first end 20 of the needle cannula 18 can include a patient end and the second end 22 of the needle cannula 18 can include a non-patient end. A sheath or pierceable cover 24 can be positioned about the second end 22 of the needle cannula 18. Engagement of the fluid collection device 12 with the second end 22 of the needle cannula 18 causes the second end 22 of the needle cannula 18 to pierce this cover and displace it in the direction of the needle hub 30 so that the second end 22 of the needle cannula 18 pierces any sealing member associated with the fluid collection device 12 and enters therein.

According to one embodiment, the fluid collection device 12 can be an evacuated specimen collection container as is known in the art having a closure assembly 14. The closure assembly 14 typically includes a resealable member or gas barrier member (not shown) for maintaining a predetermined vacuum pressure in the collection container 12. The collection container 12 can be formed from a transparent material and can be made from a material that is substantially gas-impermeable, such as glass or polyethylene terephthalate (PET). The collection container can be at least partially evacuated and is designed to maintain a desired vacuum for a considerable length of time and should accordingly have a satisfactory shelf life. Once a fluid collection procedure is completed, the collection container 12 is removed from communication with the second end 22 of the needle cannula 18. Although the resealable member of the closure assembly 14 is no longer gas impermeable after withdrawal of the needle cannula 18 therefrom, liquid impermeability is maintained by the resealable member. The collection container 12 may then be transported to an area where the fluid content of the container can be analyzed.

The package 11 can be a sterile, thermoformed blister pack and can be manufactured by any well know thermoforming processes to meet certain design requirements. According to certain configurations, the package 11 can include a first portion 40 configured for enclosing the first end 20 of the needle cannula 18, and a second portion 42 for enclosing the second end 22 of the needle cannula 18. The second portion 42 is configured for receiving the fluid collection device 12, and a transition portion 44 is positioned between the first portion 40 and the second portion 42. The transition portion 44 can be configured to secure the hub 30 therein. The second portion 42 can comprise a holder or be in the shape of a holder 16 for manipulating the needle cannula 18 during fluid collection. The second portion 42 can also have a size sufficient for holding various sized collection containers, including 13 mm and 16 mm sized tubes.

It can be appreciated that the first portion 40 of the package 11 shown in FIGS. 1, 2, and 3A-3F has different configurations, however, the particular packaging configuration can vary as is well known in the art to meet specific shipping requirements, to provide additional structure to the package, and/or to provide packaging support to various components, such as the needle cannula 18, to prevent breakage during shipping. For example, as shown in FIG. 2, safety ribs 48 can be formed integrally with a top portion 50 of the package 11 along the length of the needle cannula 18, and a bubble portion 52 (FIGS. 2 and 3A-3C) can be molded about the first end 20 of the needle cannula 18 as a protective aid to prevent inadvertent piercing of the first end 20 through the package. FIGS. 3A-3F also show various structural posts 54 and support portions 56 which provide additional support to the package 11 and/or assist with packing of a number of the packages 11 into containers for shipping. It also can be appreciated that a backing 58, as shown in FIGS. 2 and 3A-3F, can be provided which extends around the shape of the first portion 40, second portion 42, and transition portion 44, or the backing can only be provided adjacent a back portion of the first portion 40, second portion 42, and transition portion 44 and not extend from the edges thereof, as shown in FIG. 1. The top surface of top portion 50 of the package 11 can be sealed to the backing 58 along edges 60 in order to maintain the sterility of the package 11.

The first portion 40 can include a first openable region 37 and the second portion 42 can include a second openable region 38, wherein the first openable region 37 provides communication with the first portion 40 and the second openable region 38 provides communication with the second portion 42. As shown in FIG. 3D, the first openable region 37 can be bent to allow access to the first end 20 of the needle cannula 18. A bend line (not shown) can be molded or embossed into the top surface 50 of the package 11 to facilitate bending to expose this first end 20. The first and second openable regions 37, 38 can be defined by a frangible portion, such as a perforated portion, to facilitate opening thereof. The second openable region 38 can be provided in a back wall 62 of the second portion 42, as shown in FIGS. 3B-3C, wherein this openable region 38 is defined by the frangible portion and is configured to have a shape that allows for entrance of the collection container 12, therethrough. The openable region 38 can then be punched out along the frangible portion to provide access to the second end 22 of the needle cannula 18. According to another configuration, a portion of the backing 58, adjacent to the second portion 42 can be removable to enable access to and provide engagement of the collection container 12 with the second end 22 of the needle cannula 18.

With reference to FIG. 3F, the first portion 40 can be configured for shielding the first end 20 of the needle cannula 18 after use. The package 11 can include at least one undercut portion 66 configured for cooperation with the first portion 40 to snap the first portion 40, which was previously bent back to expose the first end 20 of the needle cannula 18, in place about this first end 20 of the needle cannula 18 to lock the needle cannula 18 therein and to prevent any accidental needle sticks by the first end 20 after use.

The hub 30 is secured within the package. The hub 30 can be secured by a variety of techniques including gluing, ultrasonic welding, or mechanical securing, wherein a portion of the package 11 is configured to allow for a snap fit within the transition portion 44 of the package 11.

Reference is now made to FIGS. 3A-3F which show a method of using a fluid collection set having an integrated package. As a preliminary matter, it is noted that FIGS. 3A-3C are directed to engagement of the collection container 12 with the second end 22 of the needle cannula 18, and FIGS. 3D-3F are directed to the exposure of the first end 20 of the needle cannula 18 and subsequent shielding of the first end 20 of the needle cannula 18. FIGS. 3A-3F do not necessarily depict a specific order of operation or use of the device, as typically, the first end of the needle is inserted into the specimen source, such as the vein of the patient, and subsequent to this insertion, the collection device, which is typically an evacuated container, is associated with the second end of the needle. The reason for this particular order of operation is so that the vacuum within the container acts to draw the specimen sample into the container as opposed to drawing atmospheric air into the container.

With continuing reference to FIGS. 3A-3F, the method includes providing a package 11 including a needle cannula 18 having a first end 20 and a second end 22, and a hub 30 configured for supporting the needle cannula 18, opening the package 11 at a first openable region 37 to expose the first end 20 of the needle cannula 18, inserting the first end 20 of the needle cannula 18 into a patient (not shown), opening the package 11 at a second openable region 38 and receiving a fluid collection device 12 therein. The second openable region 38 is in communication with the second end 22 of the needle cannula 18. The method further includes inserting the fluid collection device 12 into the second openable region 38, as shown in FIGS. 3B-3C, such that the closure assembly 14 engages the second end 22 of the needle cannula 18 to withdraw a fluid sample from the patient, wherein the package 11 is configured to be used as a holding device to manipulate the needle cannula 18 during fluid collection.

In certain configurations, the fluid collection device 12 comprises an evacuated specimen collection container engageable with the second end 22 of the needle cannula 18 through at least a portion of the package 11. The method further includes withdrawing the first end 20 of the needle cannula 18 from the patient and closing the package 11, as shown in FIGS. 3E-3F to shield the first end 20 of the needle cannula 18 therein for disposal. The package 11 can include undercut portions 66 adjacent the first end 20 of the needle cannula 18 to at least partially trap this first end 20 of the needle cannula 18 inside the package 11 after use. The package 11 can comprise a sterile, thermoformed blister pack and the second end 22 of the needle cannula can include a sheath or pierceable sleeve 24 thereon. The hub 30, supporting the needle cannula 18, is secured within the package 11 during packaging and remains secured therein during disposal.

In accordance with another embodiment of the present invention, a method of forming a fluid collection set 10 includes thermoforming a blister pack or package 11 defining a first portion 40, a second portion 42, and a transition portion 44 located between the first portion 40 and the second portion 42, providing a needle hub 30 supporting a needle cannula 18 wherein the needle cannula 18 has a first end 20 and a second end 22, and securing the needle hub 30 within the transition portion 44 of the blister pack 11 such that the first end 20 of the needle cannula 18 extends within the first portion 40 of the blister pack 11 and the second end 22 of the needle cannula 18 extends within the second portion 42 of the blister pack 11. The first portion 40 has a shape configured to enclose the first end 20 of the needle cannula 18 and the second portion 42 has a shape configured to receive a fluid collection device 12 therein and function as a needle holder 16 to enable manipulation of the needle cannula 18 during fluid collection. The second portion can be sized to accommodate various sized collection containers 12 including 13 mm and 16 mm evacuated tubes. The method further includes providing a first frangible portion or openable region 37 adjacent an end 41 of the first portion 40 wherein the first frangible portion 37 is configured to expose the first end 20 of the needle cannula 18 and providing a second frangible portion or second openable region 38 adjacent an end 43 of the second portion 42 wherein the second frangible portion 38 is configured to receive the fluid collection device 12 therein. The method can also include providing at least one undercut portion 66 in the first portion 40 configured to cooperate with the blister pack 11 to enclose the first end 20 of the needle cannula 18 after use for disposal of the used fluid collection set 10.

The present invention provides for a needle collection set having an integrated package which is a sterile barrier system that is extremely low in cost to manufacture and it eliminates a molded holder, eliminates a safety shield, and eliminates assembly of these components.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of this description. For example, it is to be understood that the present invention contemplates that, to the extent possible, one or more features of any embodiment can be combined with one or more features of any other embodiment.

The invention claimed is:

1. A fluid collection set having an integrated package comprising:
   a double-ended needle cannula having a first end and a second end;
   a hub for supporting the needle cannula;
   an integrated package at least partially enclosing the needle cannula and the hub, the package including a first openable region and a second openable region, the second openable region defined by frangible portion, the second openable region configured for receiving a fluid collection device therein, wherein the first openable region comprises a bendable portion bendable from an initial position to open the first openable region to enable a first end of the needle cannula to extend through the first openable region during fluid collection, wherein the package is configured to be used as a holder to manipulate the needle cannula at least a portion of which is contained within the package during fluid collection, wherein the first openable region is configured to bend back to the initial position after fluid collection, the package including at least one undercut portion configured for cooperation with the first openable region to lock the first end of the cannula within the package after fluid collection, wherein the package comprises a first portion for enclosing at least the first end of the needle cannula, a second portion for enclosing at least the second end of the needle cannula, the second portion including a back wall and wherein the second openable region comprises a frangible portion in the back wall having a shape configured for receiving the fluid collection device therethrough, and a transition portion positioned between the first portion and the second portion, wherein the hub is secured within the transition portion.

2. The fluid collection set of claim 1 wherein the first end of the cannula comprises a patient end and a second end of the cannula comprises a non-patient end.

3. The fluid collection set of claim 2, further comprising an evacuated specimen collection container engageable with the second end of the needle cannula through at least a portion of the package.

4. The fluid collection set of claim 3 wherein the evacuated specimen collection container is engageable through the second openable region.

5. The fluid collection set of claim 1 wherein the package comprises a sterile, thermoformed blister pack.

6. The fluid collection set of claim 1 wherein the second portion comprises the holder for manipulating the needle cannula during fluid collection.

7. The fluid collection set of claim 6 wherein the first portion includes the first openable region and the second portion includes the second openable region, wherein the first openable region provides communication with the first portion and the second openable region provides communication with the second portion.

8. The fluid collection set of claim 1 wherein the hub is secured within the transition portion by gluing, welding, or mechanical securing.

9. The fluid collection set of claim 1, wherein a bend line is formed in a top surface of the package to facilitate bending of the first openable region to provide access to the first end of the needle cannula, and wherein the first openable region is configured to bend back along the bend line to the initial position to enclose the first end of the needle cannula after fluid collection.

10. The fluid collection set of claim 1, including safety ribs formed integrally with a top portion of the package, wherein the safety ribs extend in a perpendicular direction with respect to a longitudinal length of the needle and across a top surface of the needle along the longitudinal length of the needle cannula such that the safety ribs are positioned between the top portion of the package and the needle.

11. The fluid collection set of claim 10, wherein the top portion of the package includes a bubble portion at a location adjacent to the first end of the needle cannula.

12. The fluid collection set of claim 1, wherein the package includes structural posts and support portions.

13. A fluid collection set having an integrated package comprising:
    a double-ended needle cannula having a first end and a second end;
    a hub configured for supporting the needle cannula;
    an integrated package at least partially enclosing the needle cannula and the hub, the package including a first openable region and a second openable region, the second openable region configured for receiving a fluid collection device therein, wherein the first openable region comprises a bendable portion bendable from an initial position to open the first openable region to enable a first end of the needle cannula to extend through the first openable region during fluid collection, wherein the package is configured to be used as a holder to manipulate the needle cannula at least a portion of which is contained within the package during fluid collection, wherein the first openable region is configured to bend back to the initial position after fluid collection, the package including at least one undercut portion configured for cooperation with the first openable region to lock the first end of the cannula within the package after fluid collection, wherein the package includes a top portion sealed to a backing along an edge and wherein at least a portion of the backing is removable from the top portion along the edge to provide access to the second end of the needle cannula or to the fluid collection device, and wherein the package comprises a first portion for enclosing at least the first end of the needle cannula, a second portion for enclosing at least the second end of the needle cannula and for receiving the fluid collection device, and a transition portion positioned between the first portion and the second portion, wherein the hub is secured within the transition portion.

14. The fluid collection set of claim 13, including safety ribs formed integrally with the top portion of the package, wherein the safety ribs extend in a perpendicular direction with respect to a longitudinal length of the needle and across a top surface of the needle along the longitudinal length of the needle cannula such that the safety ribs are positioned between the top portion of the package and the needle.

15. The fluid collection set of claim 13, wherein the top portion of the package includes a bubble portion at a location adjacent to the first end of the needle cannula.

16. The fluid collection set of claim 13, wherein the package includes structural posts and support portions.

17. The fluid collection set of claim 13, wherein the second portion comprises the holder for manipulating the needle cannula during fluid collection.

18. The fluid collection set of claim 13, wherein the hub is secured within the transition portion by gluing, welding, or mechanical securing.

\* \* \* \* \*